Figure 1:
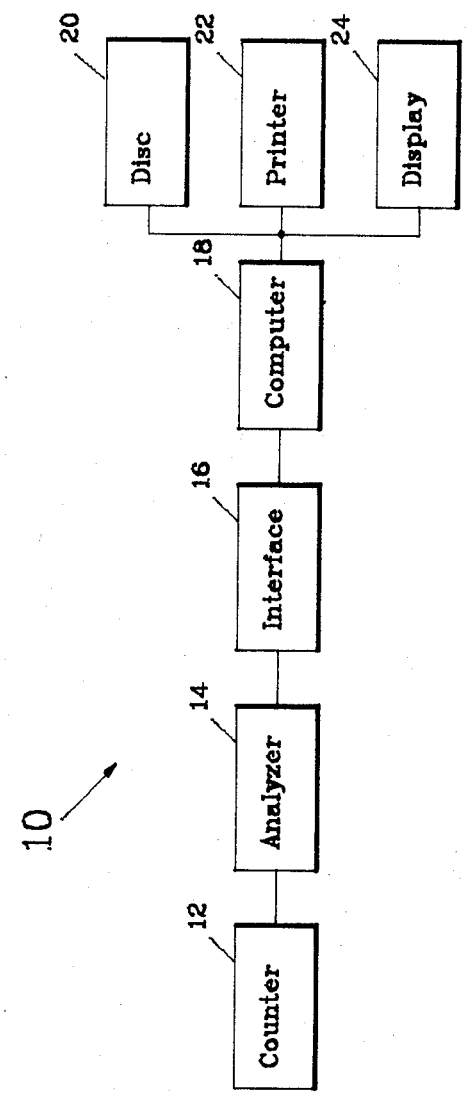

United States Patent [19]

Pasula

[11] Patent Number: 4,614,722

[45] Date of Patent: Sep. 30, 1986

[54] METHOD AND APPARATUS FOR MEASURING THE DEGREE OF REACTION BETWEEN ANTIGENS AND LEUKOCYTE CELLULAR ANTIBODIES

[76] Inventor: Mark J. Pasula, 369 NE. 116 St., Miami, Fla. 33161

[21] Appl. No.: 547,767

[22] Filed: Nov. 1, 1983

[51] Int. Cl.$^4$ .................... G01N 33/566; A61K 39/36
[52] U.S. Cl. ...................................... 436/501; 424/91; 436/63; 436/513; 436/519
[58] Field of Search ................ 324/71.1, 71.2; 377/10, 377/11, 12; 436/501, 513, 519, 63; 424/91

[56] References Cited

U.S. PATENT DOCUMENTS

| | | | |
|---|---|---|---|
| 3,836,849 | 9/1974 | Coulter et al. | 324/71.1 |
| 3,949,198 | 4/1976 | Coulter et al. | 377/12 |
| 4,236,893 | 12/1980 | Rice . | |
| 4,286,963 | 9/1981 | Ledis et al. . | |
| 4,294,817 | 10/1981 | Burgett et al. . | |
| 4,346,018 | 8/1982 | Carter et al. . | |
| 4,374,644 | 2/1983 | Armstrong | 436/63 |
| 4,485,175 | 12/1984 | Ledis et al. | 436/63 |

OTHER PUBLICATIONS

Augustin, R., Handbook of Experimental Immunology, 3rd ed., (1978), pp. 45.52–45.53, Blackwell Scientific Pub.

N. T. K. Bryan et al., Cytotoxic Reactions in the Diagnosis of Food Allergy, 4 Otolaryngologic Clinics of North America, (No. 3), pp. 523–534, (Oct. 1971).

"Food Can Change Your Mood", by Stuart Berger, M.D. published in *Parade Magazine*, Dec. 23, 1984.

"Recent Advances in Hay Fever Research are Nothing to Sneeze About", by Susan V. Lawrence published in *Smithsonian*.

"Food Allergies", published in *The Medical Forum*, Dec. 1983, vol. 9, No. 2, pp. 3 and 4.

"Cytotoxic Reaction in the Diagnosis of Food Allergy", *Symposium on Allergy in Otolaryngolic Practice*, W. T. K. Bryan, A. B. Bryan, pp. 523–533.

*Instruction Manual for the Coulter Counter Model ZM*, Oct. 1982, pp. 1-1 to 2-6.

"The Flaw in Cytotoxic Testing: There's No Proof That it Works", by Richard C. Thompson.

*Federal Register*, vol. 48, No. 162, Friday Aug. 19, 1983, pp. 37716–37722.

"Cytotoxic Testing", published in *Talk Paper*, by Bruce Brown, Jul. 6, 1984, pp. 1 and 2, (FDA).

Primary Examiner—Christine M. Nucker
Assistant Examiner—Stephen C. Wieder
Attorney, Agent, or Firm—Roger S. Thompson

[57] ABSTRACT

Method and apparatus for the objective determination of the degree of reaction between a suspected allergen and a blood sample, by comparing the number and/or size-distribution of white blood cells present in the blood sample before and after reaction thereof with the suspected allergen.

17 Claims, 2 Drawing Figures

METHOD AND APPARATUS FOR MEASURING THE DEGREE OF REACTION BETWEEN ANTIGENS AND LEUKOCYTE CELLULAR ANTIBODIES

This invention relates to the field of antigen/leukocyte cellular antibody reactions; and more particularly to a method and an apparatus for the indirect determination of the level of cellular antibodies present in human blood, and the degree of reaction (if any) between a suspected allergen and the leukocyte cellular antibodies present in the blood of a particular individual.

Allergies are common and debilitating afflictions which touch the lives of millions of people the world over. The basic bodily reactions which comprise the allergic reaction are well-known and understood.

When an assimilated amino acid, or antigen (hereafter referred to generally as a "substance"), enters the body, the body's immune defense system identifies it as being either harmful (i.e. the substance is a "toxin" or an "allergen"), or as not harmful (i.e. the substance is "neutral"). If the substance is identified as neutral, then the body does not react in any extraordinary fashion. If, however, the substance is identified as an allergen, the body reacts to protect itself by creating specific cellular antibodies which will combat the intruding allergen.

In this instance, I have observed that the body's first reaction is to enlarge the white blood cells (leukocytes), increasing their internal pressure, and thereby destroying the outer cell membrane wall of the white blood cell, which allows the cell's contents to extrude. This is the observed reaction of the white blood cells to the allergen. The primary known method of testing the antigen/antibody reaction is known as "cytotoxic testing" and is described in detail in W. T. K. Bryan et al., *Cytotoxic Reactions in the Diagnosis of Food Allergy*, 4 Otolaryngologic Clinics of North America (No. 3), pp. 523-34 (October 1971). Essentially, this method comprises mixing a sample of the patient's blood cells with a small amount of dried extract of a suspected allergen which has been pre-dried on a microscope slide. This mixture is allowed to react for approximately two hours, and is then observed. The degree of reaction (if any) between the suspected allergen and the white blood cells is directly observed, and the degree of reaction therebetween is then judged subjectively by a trained technician who decides whether the condition of the few observed cells indicates the occurrence of an allergic reaction. The accuracy of this test therefore depends entirely upon the abilities and talents of the individual technician performing the test. Since the test is subjective, therefore, its reliability will depend on the quality of the training imparted to the technician, and so the results may well vary from technician to technician. It is noted that it may take a prolonged instructional period to properly train a technician to perform a cytotoxic test such as described. Accordingly, this subjective nature of the test is extremely undesirable, as it is unreliable and may lead to inaccuracies.

It is thus an object of the invention to provide a method and an apparatus for the objective determination of the degree of reaction between a suspected allergen and the white blood cells of a patient.

It is a further object of the invention to provide such an improved method and apparatus where accuracy and reliability will not depend upon the subjective interpretation of microscopic reactions by a technician.

It is also an object of the invention to obtain reactions of thousands of white blood cells as opposed to limited microscopic readings. This will give us a broader scope of the averages; and to obtain a specific size-distribution of the normal size cellular distribution.

It is yet another object of this invention to obtain results of the test based on the count of thousands of white blood cells, and to obtain a direct measurement of destruction as well as a cellular shift of the white blood cells in the presence of the antigen.

In accordance with these and other objects of the invention there is provided a method for the objective determination of the degree of reaction between a suspected allergen and at least one blood sample, the method including the steps of: counting the number of white blood cells of a first blood sample; mixing a second blood sample and the suspected allergen; counting the number of white blood cells of the mixture; and comparing the number of white blood cells of the first blood sample and of the mixture.

In a specific embodiment of the invention, there may be provided a counter for counting the number of white blood cells in a first, control, blood sample and also in a second blood sample having a suspected allergen mixed therewith, and having an output including the results of each count; an analyzer coupled to the output of the counter for analyzing those outputs to generate a size-distribution of the white blood cell counts performed by the counter; comparison means coupled to the analyzer for comparing the counts of the first and second blood samples and their respective size-distributions, to thereby determine if the suspected allergen has caused an allergic reaction.

Figure 2:
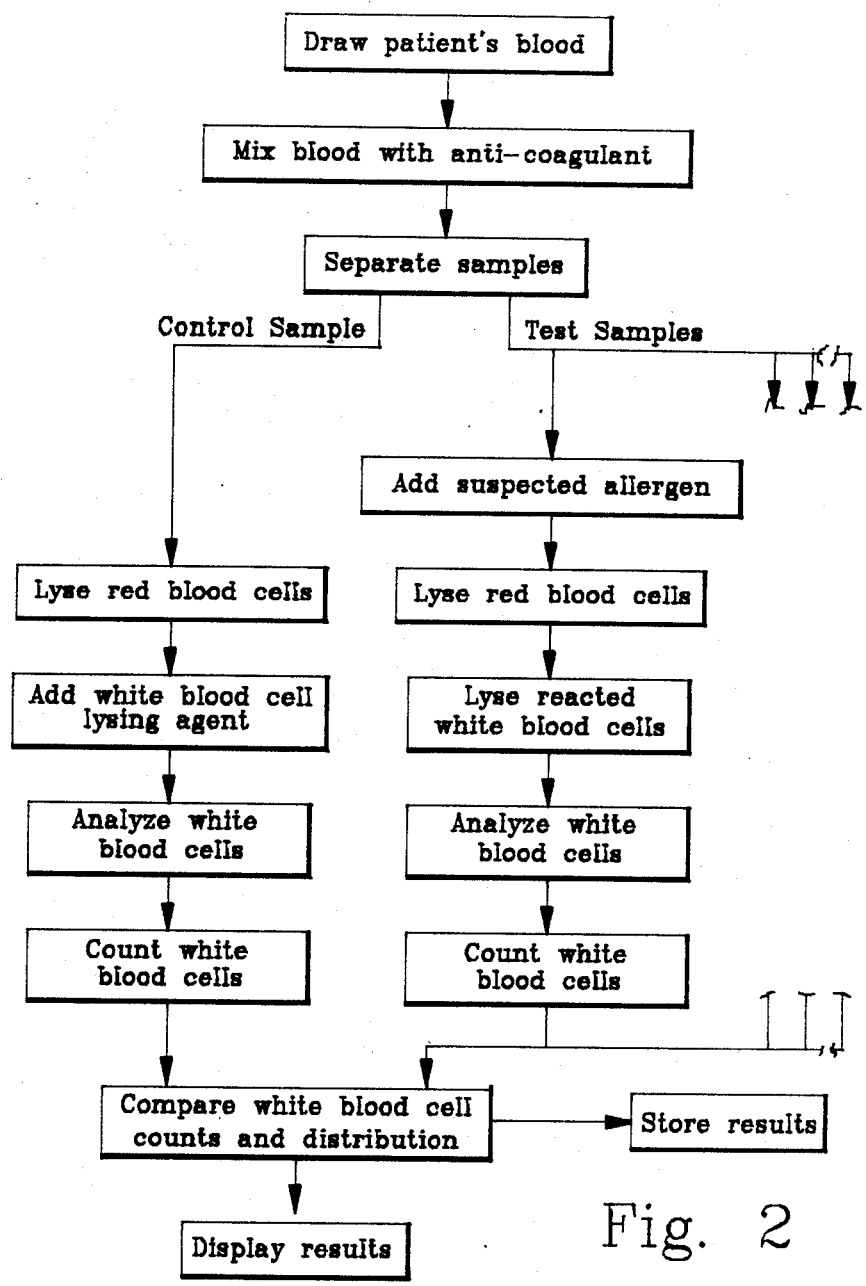

The above brief description, as well as further objects, features and advantages of the present invention, will be more fully understood by reference to the following detailed description of a preferred, but nonetheless illustrative, embodiment of the present invention, when taken in conjunction with the accompanying drawing, wherein:

FIG. 1 is a block diagram showing the connection of the various components which make up the inventive apparatus; and FIG. 2 is a flow chart showing the steps of the inventive method.

As shown in FIG. 1, the inventive apparatus 10 comprises a counter 12, an analyzer 14, a computer interface 16 and a computer 18, each connected in series, and a disc 20, a printer 22 and a display 24 each connected to the output of computer 18.

To commence the operation of the inventive apparatus (generally shown in FIG. 2.) the user thereof must first obtain a blood sample from the person being tested (subject). Preferably, the user will draw 10 cc of oxalated blood from the subject, using sodium citrate as an anticoagulant (i.e. the blood is stored in blue top B-D brand vacutainers) to prevent clotting of the blood during the test.

In order to secure an even cellular distribution over the entire volume of the blood sample, it is necessary to transfer blood from the vacutainer to an apparatus (not shown) which will have the capability of continuous slow circulation, in known fashion.

It is preferred that a single blood sample drawn from the patient be used during a battery of tests for a number of allergies, and so the blood will be separated into a plurality of smaller samples for testing. The preferred method of separation is to place 100 microliters of the blood into a receptacle containing an appropriate suspension medium, e.g. either 10 cc or 20 cc of Isoton-II (manufactured by Coulter Electronics Ltd.). The precise amount of Isoton-II used is not critical, except that the same amount should be used throughout the test, i.e. in each sample of the same blood. This will ensure that measurements taken for the test and control samples may be directly compared by virtue of the fact that they both have the same number of white blood cells and volume.

At this point, each sample will contain a mixture of Isoton-II and whole blood, which in turn includes white blood cells, red blood cells and platelets. The only particles which are of importance to the studied reaction, however, are the white blood cells, and so it is important that counter 12 only count those cells. In the preferred embodiment counter 12 is Coulter Counter Model Z-M, which may be set to count the number of particles within a given size range. Thus, since platelets are much smaller than white blood cells, it is simple to avoid counting them by setting the minimum particle size at a size greater than that of platelets, and less than that of white blood cells, for example 48 microns.

To avoid counting red blood cells, which are of roughly comparable size to the white blood cells, it is preferred that those cells be eliminated. This is preferably accomplished by adding a substance which will immediately cause red blood cells to disintegrate (a "lysing" substance), for example Zapoglobin II (Coulter). Alternatively, the red blood cells may be mechanically removed from the sample. After the red blood cells are eliminated, and counter 12 is set to the predetermined minimum size level, counter 12 may be used to count and size the white blood cells of a first sample. This first sample is used as a control sample, as it has had no suspected allergen introduced thereto.

The remaining ("test") samples of blood are treated similarly, except that the test samples have the suspected allergens added thereto. Presently known lysing agents may be dangerous to white blood cells, and so the following procedure is at this time preferred:

Step I—100 microliters of the patient's blood is introduced to a predetermined amount of suspension medium. Because of the continuous mixing of the blood, each 100 microliters thereof shall have a practically identical count and cellular size distribution.

Step II—100 microliters of a premixed food extract is added to the test sample. Nothing is added to the control sample. Both samples are allowed to stand for 60 minutes.

Step III—Using Zapoglobin II we lyse red blood cells. Using Lyse-S-II, Lyse-S-III or Acid Lyse (all Coulter), we lyse reacted white blood cells without destruction of normal non-reacted white blood cells. It is preferred to use 50 microliters or more of the agent, depending upon the number of white blood cells counted in the control sample, and a 100 microliter mixture of Lyse-S-II and Lyse-S-III is generally satisfactory for normal white blood cell levels.

Step IV—30 seconds after lysing, we take reading of the white blood cell count and the cellular distribution.

The food extract of the suspected allergen is prepared by adding 100 mg of dried extract to 10 ml of Isoton II or III (or any mixture thereof) or in 10 ml of injectable paragen-free, sterilized water. This mixture is then allowed to stand for 24 hours at room temperature, and then filtered through a mesh capable of filtering solid particles. Suitable extracts are manufactured by Hollister Steel Co., and suspected allergens prepared as described may be stored at 4 degrees centigrade (c) for ten days. The ten cubic centimeters of drawn blood prepared as described will be suitable for approximately 75 tests.

At this point, the test sample may be introduced to counter 12 and the number of white blood cells therein may be counted.

The output of counter 12 is read visually, to determine if the number of white blood cells in the test sample is less than that of the control (indicating positive reaction) or it may be input to analyzer 14, such as the Coulter Channelyzer, to obtain cellular population distributions of the number of white blood cells present in each of a plurality of size-distribution ranges. This is referred to as "sizing".

The output of analyzer 14 may also be input to computer 18 through interface 16, in known fashion, to store the data and automatically compare the results of the count of each test sample to that of the control sample as well as the size-distribution of the white blood cells. If the number of white blood cells in a test sample is less than that of the control by more than the error factor of counter 12, then there is a positive reaction. Also, if the comparison of the size-distribution results indicate enlargement of white blood cells, then there is also a positive reaction. Once all comparisons are made, the output of computer 18 may be displayed by any output means desired, such as printer 22 or video display 24, and may also be stored on disc 20 for future reference.

In this fashion, it may be objectively determined if the patient has an allergic reaction to any of the tested substances.

As will be readily apparent to those skilled in the art, the above description represents the preferred, but nonetheless illustrative, embodiment of the invention, which may be realized in other specific forms without departing from its spirit or essential characteristics. For example, the entire apparatus may be automated so that once the sample of white blood cells is drawn from the patient there need be no further human intervention or action unitl the results are complete. Therefore, the full scope of such invention is to be measured by the appended claims, giving thereto the full range of equivalence which comes within the measuring and range of the claims.

I claim:

1. A method for determining the degree of reaction between an antigen and at least a first and a second blood sample drawn from a single source, the method comprising the steps of:

counting a number of white blood cells in said first blood sample;

mixing said antigen with said second blood sample to form a mixture, and thereby allow said antigen to react with said white blood cells of said second blood sample;

counting a number of unreacted and reacted white blood cells in said mixture; and comparing said number of said white blood cells counted in said first blood sample with said number of unreacted and reacted white blood cells counted in said mixture, to determine thereby if said antigen has reacted with said white blood cells in said second blood sample.

2. The method of claim 1, further comprising the step of:
   lysing a portion of any red blood cells present in said first blood sample prior to counting said number of white blood cells therein.

3. The method of claim 1, further comprising the step of:
   lysing a portion of any red blood cells present in said mixture prior to counting said number of unreacted and reacted white blood cells therein.

4. The method of claim 1, further comprising the step of:
   lysing a portion of said reacted white blood cells in said mixture prior to counting said number of unreacted and reacted white blood cells therein.

5. The method of claim 1, wherein said counting a number of white blood cells of at least one of said first blood sample and said mixture is performed by counting a number of white blood cells within each of a plurality of varying size-distribution ranges.

6. The method of claim 5, further comprising the step of:
   producing a graph showing said number of white blood cells counted in each size range.

7. A method for determining the degree of reaction between at least one antigen and a sample of a patient's blood, the method comprising the steps of:
   separating said sample into a control sample and at least one test sample, each of said control sample and said at least one test sample having approximately equal distributions of white blood cells therein;
   lysing a portion of any red blood cells in said control sample;
   counting a number of white blood cells in said control sample;
   mixing said antigen with said at least one test sample to form a mixture, and thereby allow said antigen to react with said white blood cells present in said at least one test sample, and forming reacted white blood cells in said mixture if said patient is sensitive to said antigen;
   lysing a portion of any red blood cells in said mixture;
   lysing a portion of said reacted white blood cells in said mixture;
   counting a number of unreacted and reacted white blood cells in said mixture;
   comparing said number of unreacted and reacted white blood cells in said mixture with said number of white blood cells in said control sample, to determine thereby if said antigen has caused a reaction with said sample of a patient's blood.

8. The method of claim 7, wherein said counting said number of white blood cells in said control sample and said counting the number of unreacted and reacted white blood cells in said mixture are performed by counting a number of white blood cells within each of a plurality of varying size-distribution ranges therein, and
   generating a size-distribution graph showing a size-distribution of white blood cells in each of said control sample and said mixture;
   comparing said size-distribution graph showing said size-distribution of said white blood cells in said control sample with said size-distribution graph showing said size-distribution of white blood cells in said mixture;
   whereby a positive reaction is indicated by a significant difference therebetween.

9. The method of claim 7, wherein the determination of whether said at least one antigen has caused a reaction with said sample of a patient's blood is positive when said number of unreacted white blood cells counted in said mixture is less than said number of white blood cells counted in said control sample by an amount greater than an error factor of the equipment used.

10. A method for determining the degree of reaction between an antigen and at least one blood sample, the method comprising the steps of:
    sizing a number of white blood cells in a first blood sample;
    mixing said antigen with a second blood sample to form a mixture, and thereby allow said antigen to react with white blood cells of said second sample;
    sizing a number of unreacted and reacted white blood cells in said mixture; and
    comparing said sized white blood cells of said first blood sample with said sized unreacted and reacted white blood cells of said mixture, to determine thereby if said antigen has reacted with said white blood cells in said second sample, whereby a positive reaction is indicated by a significant difference therebetween.

11. The method of claim 10, further comprising the step of:
    lysing a portion of any red blood cells present in said first blood sample prior to sizing said white blood cells therein.

12. The method of claim 10, further comprising the step of:
    lysing a portion of any red blood cells present in said second blood sample prior to sizing said unreacted and reacted white blood cells therein.

13. The method of claim 10, further comprising the step of:
    lysing a portion of said reacted white blood cells in said mixture prior to sizing said unreacted and reacted white blood cells therein.

14. The method of claim 10, wherein said sizing of said white blood cells in a first blood sample and said sizing of said unreacted white blood cells in said mixture are performed by counting a number of white blood cells within each of a plurality of varying size-distribution ranges.

15. A method for determining the degree of reaction between at least one antigen and a sample of a patient's blood, the method comprising the steps of:
    separating said sample into a control sample and at least one test sample, each of said control sample and said at least one test sample having approximately equal distributions of white blood cells therein;
    lysing a portion of red blood cells in said control sample;
    sizing said white blood cells in said control sample thereby generating a size distribution of said white blood cells in said control sample; p1 mixing said at least one antigen with said at least one test sample to form a mixture, and thereby allow said at least one antigen to react with white blood cells present in said at least one test sample;
    lysing a portion of any red blood cells in said mixture;
    lysing a portion of any reacted white blood cells in said mixture;
    sizing said white blood cells in said mixture thereby generating a size distribution of said white blood cells in said mixture; and comparing said size distribution of said white blood cells in said mixture with said size distribution of said white blood cells in said control sample, and thereby determine if said at least one antigen has caused a reaction with said sample of a patient's blood.

16. The method of claim 15, wherein said sizing of said white blood cells in said control sample and said mixture is performed by counting a number of said white blood cells within each of a plurality of varying size-distribution ranges, and generating a size-distribution of the counts of each of said control sample and said mixture; and comparing said size-distribution of said white blood cells in said control sample with said size-distribution of said white blood cells in said mixture.

17. The method of claim 15, wherein the determination of whether said at least one antigen has caused an allergic reaction with said sample of a patient's blood is positive when said size-distribution of said white blood cells in said mixture differs from said size-distribution of said white blood cells in said control sample to a degree greater than an error factor of the equipment used.

* * * * *